（12）United States Patent
Stampanoni et al.

(10) Patent No.: US 9,700,275 B2
(45) Date of Patent: Jul. 11, 2017

(54) QUANTITATIVE X-RAY RADIOLOGY USING THE ABSORPTION AND SCATTERING INFORMATION (71) Applicant: PAUL SCHERRER INSTITUT, Villigen PSI (CH)

(72) Inventors: Marco Stampanoni, Endingen (CH); Zhentian Wang, Brugg (CH)

(73) Assignee: PAUL SCHERRER INSTITUT, Villigen PSI (CH)

( * ) Notice: Subject to any disclaimer, the term of this patent is extended or adjusted under 35 U.S.C. 154(b) by 59 days.

(21) Appl. No.: 14/890,006

(22) PCT Filed: Apr. 25, 2014

(86) PCT No.: PCT/EP2014/058501
§ 371 (c)(1),
(2) Date: Nov. 9, 2015

(87) PCT Pub. No.: WO2014/180683
PCT Pub. Date: Nov. 13, 2014

(65) Prior Publication Data
US 2016/0113611 A1  Apr. 28, 2016

(30) Foreign Application Priority Data
May 10, 2013  (EP) .................................... 13167288

(51) Int. Cl.
*G01N 23/207* (2006.01)
*A61B 6/04* (2006.01)
(Continued)

(52) U.S. Cl.
CPC ............ *A61B 6/502* (2013.01); *A61B 6/4035* (2013.01); *A61B 6/483* (2013.01); *A61B 6/484* (2013.01);
(Continued)

(58) Field of Classification Search
CPC .......... G01N 23/201; G01N 23/20083; G01N 2223/423; G01N 23/203; G01N 23/06;
(Continued)

(56) References Cited

U.S. PATENT DOCUMENTS 6,054,712 A * 4/2000 Komardin .............. A61B 6/483
250/363.06
9,036,773 B2   5/2015 David et al.
(Continued)

FOREIGN PATENT DOCUMENTS

WO   2011011014 A1   1/2011
WO   2012000694 A1   1/2012
(Continued)

OTHER PUBLICATIONS

Wang, Zhen-tian, et al., "Quantitative grating-based x-ray dark-field computed tomography", American Institute of Physics, Applied Physics Letters, 2009, pp. 094105, vol. 95, No. 9.

*Primary Examiner* — Don Wong
(74) *Attorney, Agent, or Firm* — Laurence Greenberg; Werner Stemer; Ralph Locher (57) ABSTRACT

A quantitative radiographic method uses X-ray imaging. The method uses a ratio of the absorption signal and the (small-angle) scattering signal (or vice-versa) of the object as a signature for the materials. The ratio image (dubbed R image) is independent from the thickness of the object in a wide sense, and therefore can be used to discriminate materials in a radiographic approach. This can be applied to imaging systems, which can record these two signals from the underlying object (for instance, an X-ray grating interferometer). Possible applications could be in material science, non-destructive testing and medical imaging. Specifically, the method can be used to estimate a volumetric breast (Continued)

density. The use of the R image and the corresponding algorithm are also presented hereafter.

25 Claims, 7 Drawing Sheets

(51) Int. Cl.
*G01N 23/201* (2006.01)
*A61B 6/00* (2006.01)
*G01N 23/20* (2006.01)
*G01N 23/083* (2006.01)

(52) U.S. Cl.
CPC ......... *A61B 6/5217* (2013.01); *G01N 23/083* (2013.01); *G01N 23/20083* (2013.01); *A61B 6/4291* (2013.01)

(58) Field of Classification Search
CPC ....... G01N 2223/643; G01N 2223/051; G01N 23/20091; G01N 23/22
USPC ...................... 378/45, 51, 53, 46, 86, 88, 90
See application file for complete search history.

(56) References Cited

U.S. PATENT DOCUMENTS

| | | |
|---|---|---|
| 2013/0094625 A1 | 4/2013 | Huang et al. |
| 2013/0279659 A1 | 10/2013 | Stampanoni et al. |
| 2015/0030123 A1 | 1/2015 | Stampanoni et al. |

FOREIGN PATENT DOCUMENTS

| | | |
|---|---|---|
| WO | 2012080125 A1 | 6/2012 |
| WO | 2013124164 A1 | 8/2013 |

\* cited by examiner

| Material alias | Mean value of R |
|---|---|
| PMMA | 3.55 |
| Nylon | 5.32 |
| Derlin | 4.60 |
| Teflon | 1.86 |
| PE-HD | 0.57 |

QUANTITATIVE X-RAY RADIOLOGY USING THE ABSORPTION AND SCATTERING INFORMATION

BACKGROUND OF THE INVENTION

Field of the Invention

The present invention relates to a method and a system for quantitative X-ray radiology using the absorption and the forward scattering information.

In X-ray imaging, the absorption contrast is well known to follow the Beer-Lambert law. For monochromatic beam, we have $$T = -\ln\left(\frac{I}{I_0}\right) = \int_l \mu(l)\,dl, \quad (1)$$

where $I$ and $I_0$ are the intensity signal on the detector and the incident X-rays intensity, respectively. $l$ is the direction along the path of the X-ray beam and $\mu$ is the linear attenuation coefficient of the underlying object. Practically, in medical imaging, the beam generated by X-ray tube is always rather polychromatic. In that case, the linear attenuation coefficient $\mu$ will depend on the energy of the photons. Eq. (1) becomes $$T = -\ln\left(\frac{I}{I_0}\right) = \int E(\varepsilon)\eta(\varepsilon)\exp\left(-\int_l \mu(\varepsilon,l)\,dl\right)d\varepsilon, \quad (2)$$

where $E(\varepsilon)$ is the spectrum of the X-rays, and $\eta(\varepsilon)$ is the energy response of the detector at photon energy $\varepsilon$. Eq. (2) is no longer a simple linear integral, namely the Beer-Lambert law. However, in the range of certain applications, for instance mammography, it has been shown that Eq. (1) approximately holds for polychromatic beam by theory as well as experiments [1]. Therefore, we have $$T = -\ln\left(\frac{I}{I_0}\right) = \int_l \mu_{\mathit{eff}}(\bar{\varepsilon},l)\,dl, \quad (3)$$

where $\mu_{\mathit{eff}}$ is defined as the effective attenuation coefficient at the mean energy of $\bar{\varepsilon}$. For single material, Eq. (3) can be simplified to $$T = \mu_{\mathit{eff}}(\bar{\varepsilon}) \cdot L, \quad (4)$$

where $L$ is the thickness of the sample along the X-ray beam direction.

Further, any in-homogeneities in the micro- or nanometer range within the sample will cause X-ray photons to scatter. This forward scattering concentrates in very small angles, and therefore it is called small-angle scattering. Measurements of the local small-angle scattering power can deliver important structural information about the sample, and are thus widely used in the characterization of materials. It has been shown that the small-angle scattering signal, obtained for instance by a grating interferometer or diffraction enhanced imaging, follows a similar way as the absorption signal for monochromatic beam [2], $$S = \sigma^2 = \int_l s(\varepsilon,l)\,dl, \quad (5)$$

where $\sigma^2$ is the second moment of the scattering angle distribution of the outgoing beam and $s(\varepsilon,l)$ is the generalized scattering parameter which is equivalent to the attenuation coefficient in the absorption case [3].

Usually the Gaussian scattering approximation is used to model the outgoing beam. The scattering angle distribution $p(\theta)$ is modeled by $$p(\theta) = \frac{1}{\sigma\sqrt{2\pi}}\exp\left(-\frac{\theta^2}{2\sigma^2}\right). \quad (6)$$

For polychromatic beam, the total scattering angular distribution $\bar{p}(\theta)$ will be the incoherent addition of all the $p(\theta)$ at different photon energies:

$$\bar{p}(\theta) = \int_{\varepsilon_1}^{\varepsilon_2} E(\varepsilon) p(\theta,\varepsilon)\,d\varepsilon \quad (7)$$

$$= \int_{\varepsilon_1}^{\varepsilon_2} E(\varepsilon)\frac{1}{\sigma(\varepsilon)\sqrt{2\pi}}\exp\left(-\frac{\theta^2}{2\sigma(\varepsilon)^2}\right)d\varepsilon,$$

where $[\varepsilon_1,\varepsilon_2]$ is the integration interval of the spectrum $E(\varepsilon)$. If $E(\varepsilon)$ is assumed to be a continuous function and normalized on the integration interval, then the mean value theorem of integrals indicates that $$\bar{p}(\theta) = \frac{1}{\sigma(\bar{\varepsilon})\sqrt{2\pi}}\exp\left(-\frac{\theta^2}{2\sigma(\bar{\varepsilon})^2}\right)\int_{\varepsilon_1}^{\varepsilon_2} E(\varepsilon)\,d\varepsilon \quad (8)$$

$$= \frac{1}{\sigma(\bar{\varepsilon})\sqrt{2\pi}}\exp\left(-\frac{\theta^2}{2\sigma(\bar{\varepsilon})^2}\right)$$

where $\bar{\varepsilon}$ is a constant within the range $[\varepsilon_1,\varepsilon_2]$. Eq. (8) shows that the total scattering angular distribution $\bar{p}(\theta)$ for polychromatic beam is still a Gaussian distribution. For single material, the second moment of $\bar{p}(\theta)$ is $$\sigma^2(\bar{\varepsilon}) = \int_{\varepsilon_1}^{\varepsilon_2} E(\varepsilon)\sigma^2(\varepsilon)\,d\varepsilon \quad (9)$$

$$= \int_{\varepsilon_1}^{\varepsilon_2} E(\varepsilon) s(\varepsilon) L\,d\varepsilon$$

$$= s_{\mathit{eff}}(\bar{\varepsilon}) L \int_{\varepsilon_1}^{\varepsilon_2} E(\varepsilon)\,d\varepsilon$$

$$= s_{\mathit{eff}}(\bar{\varepsilon}) \cdot L.$$

Here the mean value theorem of integrals is used again as well as the fact that the scattering angular distributions of each single energy are independent. $s_{\mathit{eff}}(\bar{\varepsilon})$ is defined as the effective scattering parameter of the materials at the mean energy $\bar{\varepsilon}$.

The linear relationship of Eq. (4) and Eq. (9) hold in a wider sense as long as the X-ray spectrum function $E(\varepsilon)$ is generally continuous and the beam hardening effect is not severe.

In conventional absorption-based radiographic methods, quantitative imaging (for instance, discriminating materials or determining the material composition) is not possible without pre-calibrations. The difficulty lies on the fact that Eq. (4) has two unknown parameters: the effective attenuation coefficient and the thickness of the sample. The same absorption value could represent arbitrary combination of the thickness and attenuation coefficient.

BRIEF SUMMARY OF THE INVENTION

It is therefore the objective of the present invention to provide a system and a method for quantitative X-ray radiology eliminating the drawback given above. It would be desirable to improve the prior art in a way that the same absorption value might be analyzed in order to identify whether the absorption information has been caused rather by the present thickness of the probe or the attenuation coefficient of the probe which allows enables the evaluation whether one material or diverse materials have been penetrated by the X-ray beam.

This objective achieved according to the present invention by the features given in the independent claims 1 for the method and 17 for the system.

The way according to the present invention to overcome this problem and get quantitative information of the sample is to involve another physical quantity in order to decouple the thickness parameter. Ideally, this quantity should be obtained with the absorption information simultaneously. This requirement will maximally reduce the errors due to imaging the specimen in different circumstances. A multiple-modality imaging system is a potential solution, such as the grating interferometer. A suitable physical quantity in this sense is the forward scattering information used simultaneously with the absorption information of the x-ray analysis.

According to the present invention, in conditions where the beam hardening effect is not severe, for instance, in medical imaging applications like mammography, Eq. (4) and Eq. (9) are both linear with the thickness L, therefore their "ratio image", which is defined as the R image here, cancels out the unknown parameter L, leading to Eq. (10):

$$R = \frac{T}{S} = \frac{\mu_{eff}(\bar{\varepsilon})L}{s_{eff}(\bar{\varepsilon})L} = \frac{\mu_{eff}(\bar{\varepsilon})}{s_{eff}(\bar{\varepsilon})}. \quad (10)$$

Since the R value doesn't depend on the thickness of the sample, naturally it can be considered as the signature of the material of the sample in the radiographic imaging. The same material is expected to show the same R value regardless from the thickness.

It is worth mentioning that the R value is not expected to be as unique as the atomic number or electron density for material discrimination purpose. For compressible samples, e.g. the glandular and fat tissue of breast in medical imaging, both their attenuation coefficient and the generalized scattering parameter might change when different compressions are applied. Therefore, the R value may also change accordingly. However, despite of these small limitations, this concept of the thickness irrelevance in the R value is useful in most medical applications.

Preferred embodiments of the present invention are given in the dependent claims 2 to 16 with respect to the method and 18 to 24 with respect to the system.

BRIEF DESCRIPTION OF THE SEVERAL VIEWS OF THE DRAWING

Preferred embodiments of the present invention are described hereinafter with reference to the attached drawings which depict in.

DESCRIPTION OF THE INVENTION

With respect to the equations given above for the calculation of the R image, the justification of Eq. (4) and Eq. (9) by experiments on several known plastic materials is given in FIG. 1. The samples were imaged using a grating interferometer with a broad spectrum like one of the grating interferometers shown in FIG. 6. FIG. 1 shows the results of the validation experiments on five plastic materials. FIG. 1(*a*) shows the phantom design; (b) is the absorption image and (c) is the scattering image: FIG. 1(*d*) shows the resulting R image. In FIG. 1(*e*) the profiles of the absorption image for the five materials are illustrated. Forty horizontal lines were used for each material (the ROI was indicated in FIG. 1(*c*)) and averaged along the vertical direction. FIG. 1(*f*) are the profiles of the scattering image for the five materials, forty horizontal lines were used for each material and averaged along the vertical direction. FIG. 1(*g*) are the profiles of the resulting R images for each material. Noticeable noises were observed at the places where the samples were too thin, especially for Nylon and Derlin. This was because the scattering signals were close to the noise level at those places. FIG. 1(*g*) is therefore truncated from the thickness of 1.2 cm as indicated by the right rectangle in FIG. 1(*d*). In FIG. 1(*h*) the tabulated R value for the five given materials is listed.

It can be seen that the R values of the five materials are independent of the thickness within a good approximation. And the materials can be easily distinguished by their R values which confirms exactly the general expectations on this techniques.

Figure 1A:
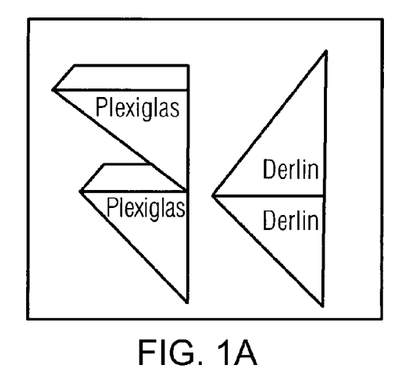
FIG. 1 results from validation experiments with the use of five different plastic materials.
Figure 1B:
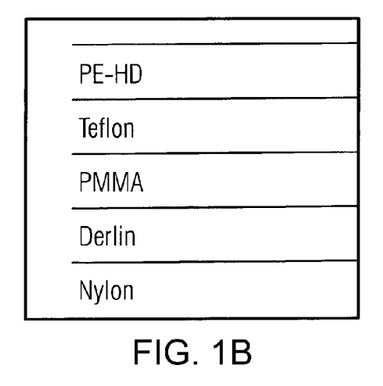
Figure 1C:
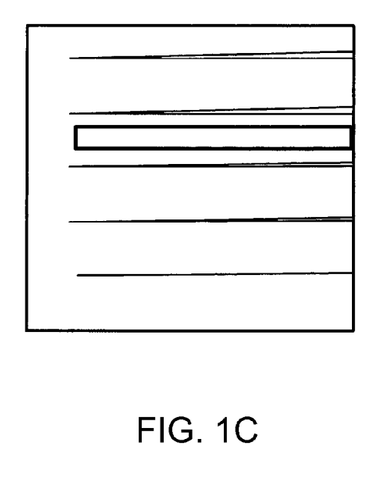
Figure 1D:
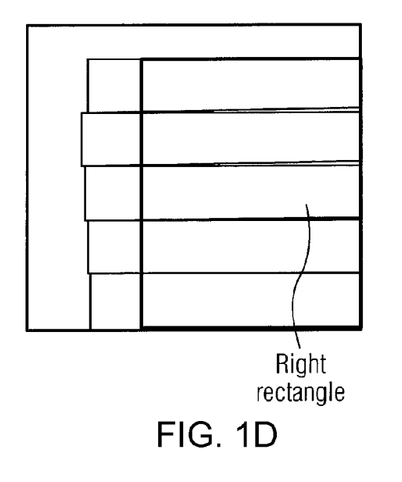
Figure 1E:
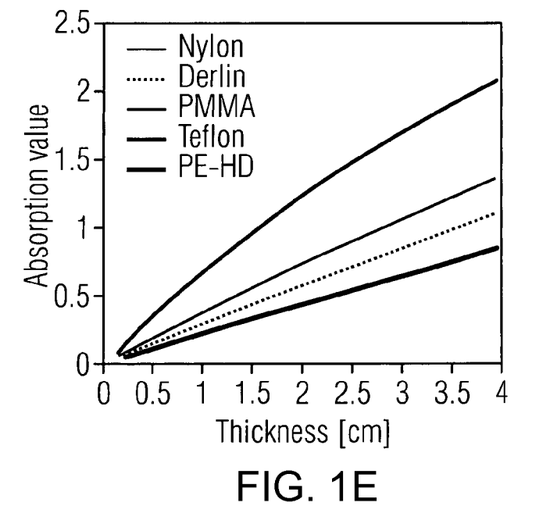
Figure 1F:
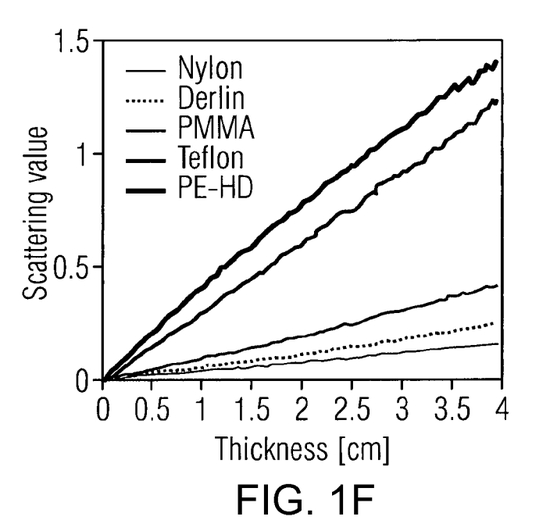
Figure 1G:
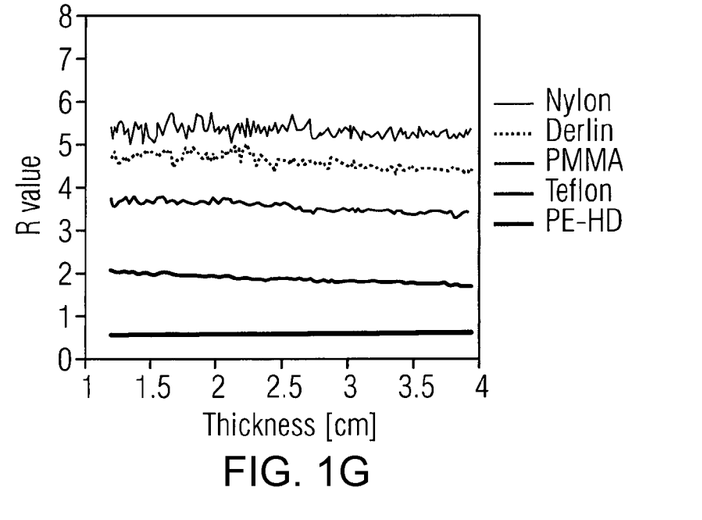
Figure 1H:
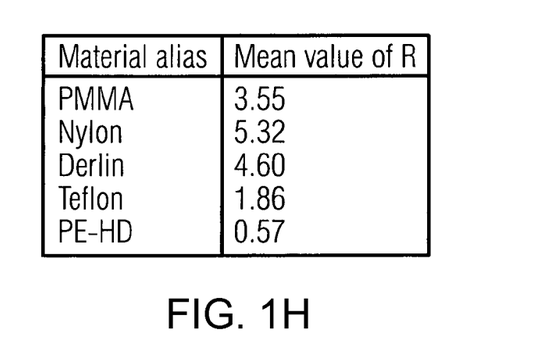
Figure 2A:
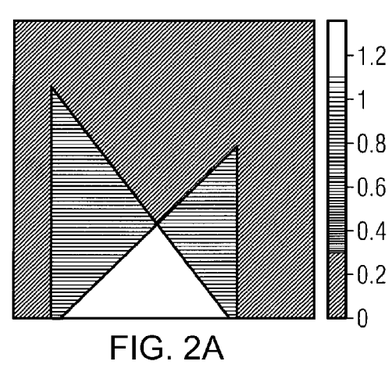
FIG. 2 results on a quantitative radiography.
Figure 2B:
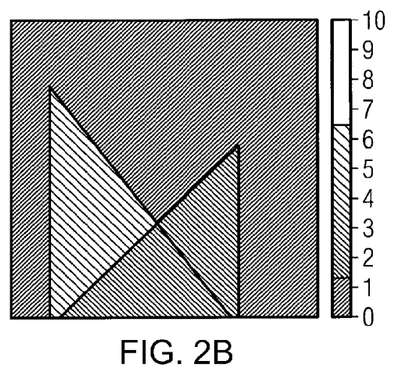
Figure 6:
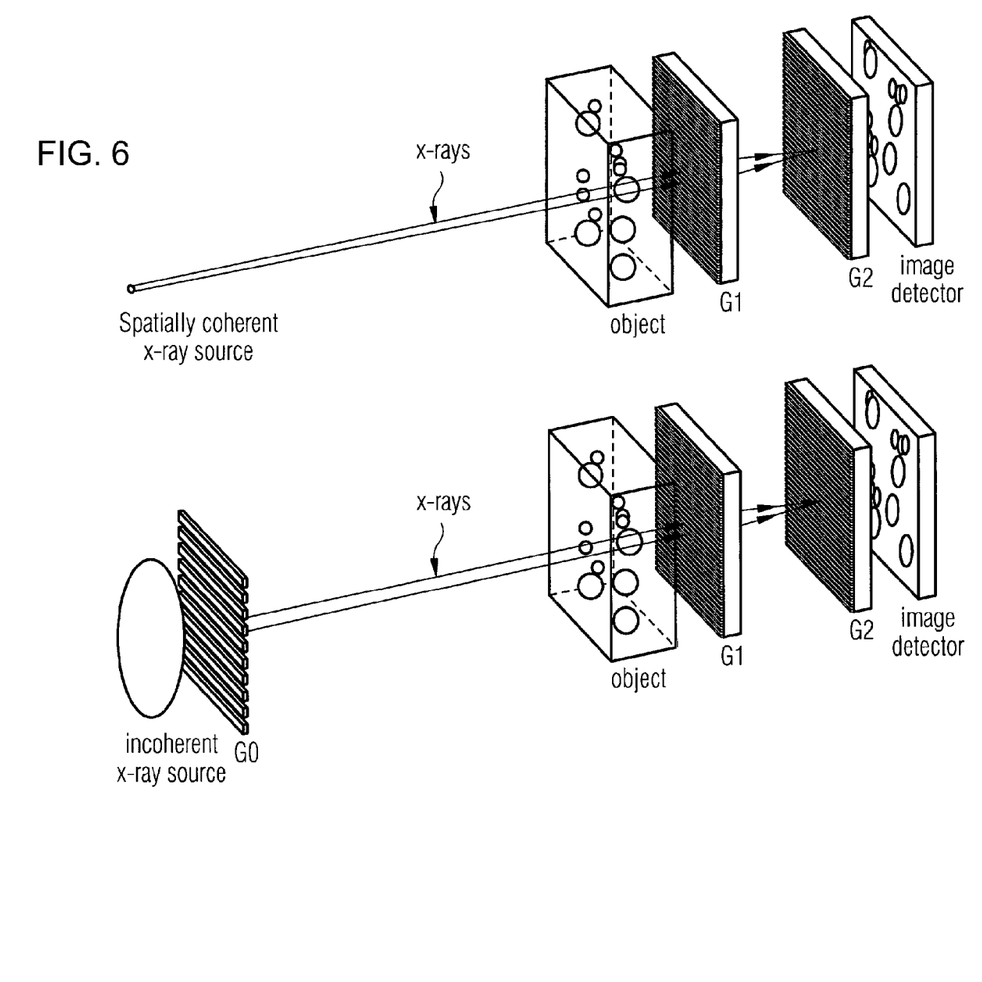
FIG. 6 a two-gratings interferometer (top) and a three-gratings interferometer (bottom) for X-ray imaging.

An application of using R image for quantitative radiology is given in FIG. 2. Conventional X-ray absorption-based radiography can only provide qualitative information (e.g. morphology) of the underlying sample, but not quantitative information, such as telling the composition of the sample. A 4 cm×3 cm wedge phantom and a 3 cm×3 cm one of the same material were overlapped with each other and imaged using a grating interferometer set up as shown in FIG. 6. The results were shown in FIG. 2. For the absorption image only (FIG. 2(*a*)), different absorption properties were observed. However, there was not enough information to tell whether it was a single material with different thicknesses or just two different materials. By taking the R image of the same sample, it was clearly shown that the phantom was composed of one material (FIG. 2(*b*)). Using the calibrated data in FIG. 1(*h*), additionally, the unknown material could be identified, which was Teflon in the present case.

Using the R image, additional quantitative information can be obtained compared to conventional absorption-based radiographic methods. A particular application in medical imaging is given below regarding volumetric breast density (VBD) estimation.

Breast density has gained increasing attentions in breast cancer screening and diagnosis because it is a strong indicator of the breast cancer risk [4, 5]. Conventional 2D breast density estimation methods have the problems of subjectivity and low inter-reader agreements [6]. Volumetric breast density (VBD) determines the breast density in a 3D manner, which provides more accurate result [7]. The R image can be used to achieve quantitative volumetric breast density (VBD) estimation in mammography.

On the pixel base, the VBD is defined by (volumetric percentage of the glandular tissue)

$$m(x, y) = \frac{L_g}{L} = \frac{L_g}{L_g + L_f}, \quad (11)$$

where $L_g$, and $L_f$ are the thicknesses of the glandular tissue and fat tissue along the X-ray beam, respectively. L is the total compression thickness of the breast. The volumetric breast density of the whole breast is given by averaging m over the whole breast region $$VBD = \frac{\sum_{x,y} m(x, y)}{N},$$

where N is the pixel numbers of the breast region.

With the two-material composition assumption of the breast, Eq. (10) is $$R = \frac{T}{S} = \frac{\mu_g L_g + \mu_f L_f}{s_g L_g + s_f L_f} = \frac{\mu_g m L + \mu_f (1-m) L}{s_g m L + s_f (1-m) L}. \quad (12)$$

Taking Eq. (11) into Eq. (12), the connection between the VBD m and the measured quantity R is setup by $$m = \frac{1}{1 - \frac{\left(\frac{R}{R_g} - 1\right)}{\left(\frac{R}{R_f} - 1\right)} \frac{\mu_g}{\mu_f}}, \quad R_g < R < R_f \quad (13)$$

where $$R_g = \frac{\mu_g}{s_g} \text{ and } R_f = \frac{\mu_f}{s_f}$$

are defined as the R values for 100% glandular tissue and 100% fat tissue, respectively. The subscripts g and f represent the glandular tissue and fat tissue, respectively. $R_g$ and $R_f$ can be determined dynamically from the histogram of the R image as described in the following sections. Note that the fat tissue has a bigger R value than the glandular tissue.

$$\frac{\mu_g}{\mu_f}$$

is a constant for a certain energy and can be determined by calibrated data [7]. For instance, $$\frac{\mu_g}{\mu_f}$$

is around 1.43 for a mean photon energy of 28 KeV.

Figure 3A:
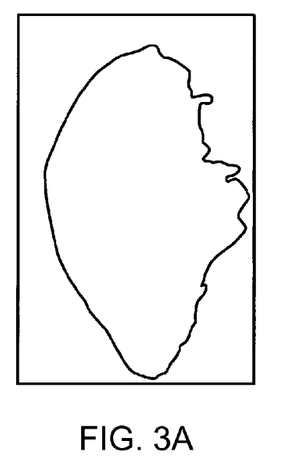
FIG. 3 an R image for one breast sample in the craniocaudal (CC) view (a) and the corresponding histogram of the R image (b)
Figure 3B:
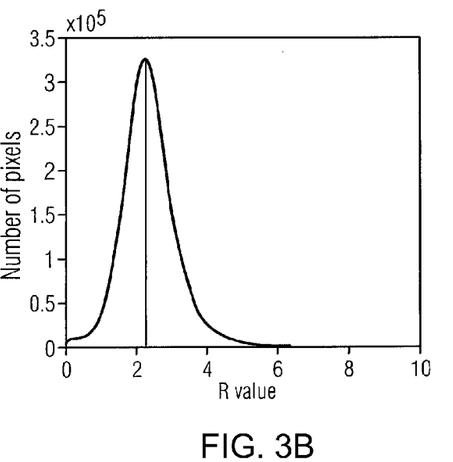

A typical histogram of the R image for the breast sample is shown in FIG. 3. FIG. 3(a) shows the R image for one breast sample in the craniocaudal (CC) view, FIG. 3(b) is the corresponding histogram of the R image. The histogram H(R) is usually an asymmetric Gaussian distribution due to the fact that the fat tissue (the right part of the histogram) is dominant in the breast compared to the glandular tissue (the left part) [8], therefore has a larger variance. The VBD information of the breast is actually implied in the asymmetric distribution of the histogram. For instance, the skewness (the third moment) of the distribution, which is defined as $$\gamma = \frac{E[(R - \mu_R)^3]}{(E[(R - \mu_R)^2])^{3/2}}, \quad (14)$$

can give a good estimation of how dominant the glandular or fat tissue is in the whole breast.

Figure 4:
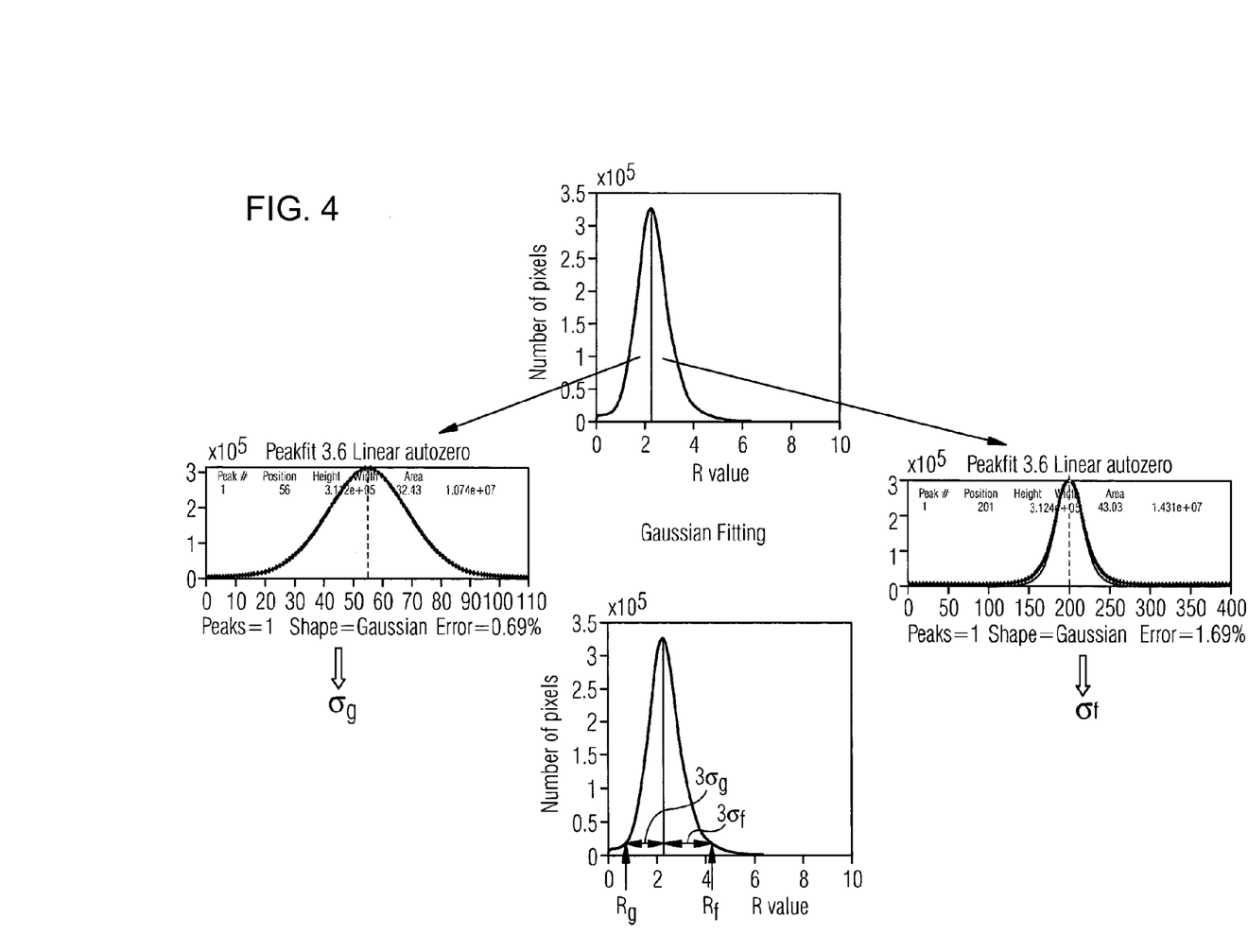
FIG. 4 a schematic illustration of the dynamic process for determining $R_g$ and $R_f$.

To get a quantitative value of the breast density from Eq. (12), we determine $R_g$ and $R_f$ in the following way with the consideration that noises always present in the R image and the dynamic process for determining $R_g$ and $R_f$ is illustrated in FIG. 4:

(1) The peak position $R_{peak}$ which gives the maximal H(R) is first decided.

(2) The histogram H(R) is divided into the left and right parts by $R_{peak}$. These two parts of the histogram are considered separately. For each half, the distribution is mirrored around the peak value to form a symmetric Gaussian distribution. Then Gaussian fitting is applied to the two resulting Gaussian distributions and their standard deviations $\sigma_g$ and $\sigma_f$ are calculated respectively.

(3) $R_g$ and $R_f$ are decided using the Nσ criteria, $$R_g = R_{peak} - N\sigma_g,$$

$$R_f = R_{peak} + N\sigma_f \quad (15)$$

where N is a positive integer. N=3 is considered to give the best approximation of the $R_g$ and $R_f$ when the noises present. The 3σ criteria covers 99.7% of the area of the histogram.

With the determined $R_g$ and $R_f$, the 3D VBD of the whole breast is calculated by weighting the normalized histogram H(R) using Eq. (15), $$VBD = \sum_R m(R) \cdot H(R). \quad (16)$$

Figure 5:
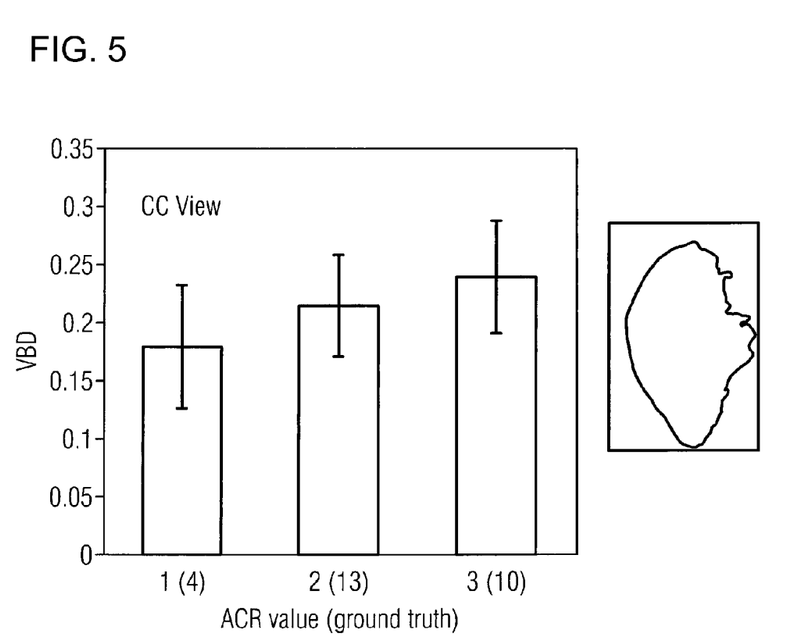
FIG. 5 the mean and standard deviation of VBD values estimated from the CC view for each diagnostic ACR group.

The proposed method was evaluated by clinical mastectomy breast dataset. 27 patients were included in the evaluation with the diagnostic breast densities: ACR 1 (4 samples), ACR 2 (13 samples), ACR 3 (10 samples) and ACR 4 (0 sample). The VBD results for the CC view using the proposed method were given in FIG. 5 which shows the mean and standard deviation of VBD values estimated from the CC view for each diagnostic ACR group. The calculated VBD values fell into the range of 10%~30% which is consistent with the previous studies using X-ray tomography and MRI [8]. A positive correlation was also clearly seen, which meant statistically the proposed method was consistent with the diagnostic results.

In this invention, the absorption and small-angle scattering signals obtained with multiple-modality systems are adopted to distinguish two types of microcalcifications. Such multiple-modality systems have been developed in the last fifteen years, including techniques based on analyzer crystal [9], gratings [10, 11, 12] and coded apertures [13, 14]. The described invention is in context with these techniques and uses the set-ups disclosed in the respective documents which form therefore part of this disclosure with respect to the set-ups.

Practical applications in non-destructive testing and medical imaging demand techniques which can work well with conventional X-ray tubes. For this reason, grating-based methods are especially promising. Without loss of generality, we will discuss the practical aspects of the method using gratings-based interferometry as an example.

Grating-based X-ray imaging setups can generate three different signals: the conventional absorption contrast (AC) signal, the differential phase contrast (DPC) signal caused by refraction due to phase shifts [11], and the small-angle scattering contrast (SC) signal (also named dark-field signal) caused by scattering from in-homogeneities in the sample [10].

Grating Interferometer set-ups with two gratings (G1 and G2) or three gratings (G0, G1, and G2) as schematically shown in FIG. 6 can be applied to record the deflection of the X-rays. In the case of a two-grating set-up, the source needs to fulfill certain requirements regarding its spatial coherence, wherein a G0 grating is required, when the source size is bigger than p2*l/d, where p2 is the period of G2, l is the distance between the source and G1, and d is the distance between G1 and G2, while in a three grating setup no spatial coherence is required [15,16]. Therefore, the three grating set-up is suited for use with incoherent X-ray sources, in particular with standard X-ray tubes for medical investigations.

To separate the conventional attenuation contrast (AC) from the DPC and SC contrast, a phase-stepping approach is applied. One of the gratings is displaced transversely to the incident beam whilst acquiring multiple images. The intensity signal at each pixel in the detector plane oscillates as a function of the displacement. The average value of the oscillation represents the AC. The phase of the oscillation can be directly linked to the wave-front phase profile and thus to the DPC signal. The amplitude of the oscillation depends on the scattering of X-rays in the object and thus yields the SC signal.

For the (two or three) gratings, several approaches have been proposed and applied. The grating G0 (if required) is the one closest to the source. It usually consists of a transmission grating of absorbing lines with the period p0. It can be replaced by a source that emits radiation only from lines with the same period [17]. The grating G1 is placed further downstream of the source. It consists of lines with a period p1. The grating G2 is the one most downstream of the setup. It usually consists of a transmission grating of absorbing lines with the period p2. It can be replaced by a detector system that has a grating-like sensitivity with the same period.

Two regimes of setups can be distinguished: in the so called "near field regime" and the "Talbot regime". In the "near field regime", the grating period p, grating distances d and the X-ray wavelength 2 are chosen such, that diffraction effects are negligible. In this case, all gratings need to consist of absorbing lines. In the "Talbot regime", diffraction from the grating structures is significant. A sharp distinction between the two regimes is not easily given, as the exact criterion depends on the duty cycle of the grating structure, and whether the gratings are absorbing or phase shifting. E.g., for a grating with absorbing lines and a duty cycle of 0.5, the condition for the "near field regime" is $d \geq p^2/2\lambda$. Here G1 should consist of grating lines that are either absorbing or, preferentially, phase shifting. Several amounts of phase shift are possible, preferentially $\pi/2$ or multiples thereof. The grating periods must be matched to the relative distances between the gratings. In the case of setups in the "Talbot regime" the Talbot effect needs to be taken into account to obtain good contrast. The formulae for the grating periods and distances are described in [18].

The sample is mostly placed between G0 and G1 (or upstream of G1 in the case of a two-grating set-up), however it can be advantageous to place it between G1 and G2 [19].

The presented invention is relevant in all of the above-mentioned cases, i.e. in the two- and three-gratings case, in the case of the "nearfield regime" and the "Talbot regime", and for the sample placed upstream or downstream of G1.

In addition, the invention presented here also works in combination with scanning-based systems as suggested in [20, 21] or for planar grating geometries, as suggested in [22].

Intensity curves (with and without sample) are usually obtained with "phase stepping" methods or alternative techniques. Defining for each pixel on the detector the mean, phase and visibility of the intensity curve with sample as $I_s$, $\Phi_s$, $V_s$, and without sample as $I_b$, $\Phi_b$, $V_b$, yields:

$$AC = -\log\left(\frac{I_s}{I_b}\right) \qquad (17)$$

$$DPC = \Phi_s - \Phi_b \qquad (18)$$

$$SC = -\log\left(\frac{V_s}{V_b}\right). \qquad (19)$$

For both the AC signal and SC signal, the valid data range is $[0,+\infty]$, while for the DPC it is $[-\pi,+\pi]$. Images obtained by plotting such signals are all perfectly registered.

A similar way to generate these multiple information signals can be found in diffraction enhanced imaging where the equivalent of the intensity curve is named the rocking curve [9].

REFERENCES

[1] J. J. Heine and M. Behera, "Effective X-ray attenuation measurements with full field digital mammography," Med. Phys. 33, 4350-4366 (2006).

[2] Z-T Wang, K-J Kang, Z-F Huang, and Z-Q Chen, "Quantitative grating-based X-ray dark-field computed tomography," Appl. Phys. Lett. 95, 094105 (2009).

[3] G. Khelashvili, J. Brankov, D. Chapman, M. Anastasio, Y. Yang, Z. Zhong, and M. Wernick, "A physical model of multiple-image radiography," Phys. Med. Biol. 51, 221 (2006).

[4] C. Byrne et al, "Mammographic features and breast cancer risk: effects with time, age, and menopause status," J. Nat. Cancer Inst. 87(21), 1622-1629 (1995).

[5] C. H. van Gils et al, "Changes in mammographic breast density and concomitant changes in breast cancer risk," *Eur. J. Cancer* 8(6), 509 (1999).

[6] A. Redondo et al, "Inter- and intraradiologist variability in the BI-RADS assessment and breast density categories for screening mammograms," *Br. J. Radiol.* 85(1019) 1465, (2012).

[7] M. J. Yaffe, "Mammographic density. Measurement of mammographic density." *Breast Cancer Res,* 10(3), 209 (2008).

[8] M. J. Yaffe, et al. "The myth of the 50-50 breast," *Medical Physics* 36(12), 5437 (2009).

[9] D. Chapman et al, "Diffraction enhanced X-ray imaging", *Physics in Medicine and Biology,* 42, 2015 (1997).

[10] F. Pfeiffer, M. Bech, O. Bunk et al., "Hard-X-ray dark-field imaging using a grating interferometer," *Nature Materials,* 7(2), 134-137 (2008).

[11] T. Weitkamp, A. Diaz, C. David et al., "X-ray phase imaging with a grating interferometer," *Optics Express,* 13(16), 6296-6304 (2005).

[12] F. Pfeiffer, C. Kottler, O. Bunk et al., "Hard X-ray phase tomography with low-brilliance sources," *Physical Review Letters,* 98(10), -(2007).

[13] A. Olivo and R. Speller, "A coded-aperture technique allowing X-ray phase contrast imaging with conventional sources", *Appl. Phys. Lett.* 91, 074106 (2007).

[14] A. Olivo and R. Speller, "Image formation principles in coded-aperture based X-ray phase contrast imaging", *Phys. Med. Biol.* 53, 6461 (2008).

[15] F. Pfeiffer, T. Weitkamp, O. Bunk et al., "Phase retrieval and differential phase-contrast imaging with low-brilliance X-ray sources," *Nature Physics,* 2(4), 258-261 (2006).

[16] C. David, T. Weitkamp, and F. Pfeiffer, [Interferometer for quantitative phase contrast imaging and tomography with an incoherent polychromatic X-ray source].

[17] C. David, [Strukturierung der Anodenoberfläche einer Röntgenröhre um eine gitterförmige Emission für die Phasenkontrastbildgebung im Röntgenbereich], (2008).

[18] T. Weitkamp, C. David, C. Kottler et al., "Tomography with grating interferometers at low-brilliance sources." *Proc. of SPIE,* 6318, 63180S (2006).

[19] C. David, [Optimierte Anordnung von Gittern für die Phasenkontrastbildgebung im Röntgenbereich], Siemens Erfindungsmeldung 2008E07939 DE (2008).

[20] C. Kottler, F. Pfeiffer, O. Bunk et al., "Grating interferometer based scanning setup for hard X-ray phase contrast imaging," *Review of Scientific Instruments,* 78(4), 043710 (2007).

[21] C. David, and F. Pfeiffer, [An interferometer for X-rays for obtaining quantitative X-ray images from an object].

[22] C. David, and M. Stampanoni, [A method for X-ray phase contrast and dark-field imaging using an arrangement of gratings in planar geometry], (2010).

The invention claimed is:

1. A method for quantitative radiology of a sample, which comprises the steps of:
   determining a material or material composition of the sample via a radiographic approach by using a ratio of an absorption signal and a small-angle scattering signal of the sample, the absorption signal and the small-angle scattering signal are obtained from an X-ray investigation based on a grating-based interferometer, analyzer-crystal-based imaging, coded aperture imaging or an imaging technique that is enabled to record both absorption signals and small-angle scattering signals.

2. The method according to claim 1, wherein the absorption signal T and the small-angle scattering signal S of the sample being a single material sample are expressed by:

$$T = -\ln\left(\frac{I}{I_0}\right) = \int_l \mu_{eff}(\bar{\varepsilon}, l)\,dl \approx \mu_{eff}(\bar{\varepsilon})\,L$$

$$S = \sigma^2 = \int_l s_{eff}(\bar{\varepsilon}, l)\,dl \approx s_{eff}(\bar{\varepsilon})\,L,$$

where $\mu_{eff}$ and $s_{eff}$ are an effective attenuation coefficient and effective generalized scattering parameter of the sample at a mean energy of $\bar{\varepsilon}$;

$\sigma^2$ is a second moment of a scattering angle distribution of an outgoing beam;

l is along a path of an X-ray beam and L is total thickness of the sample; and a ratio image, dubbed R image, is defined by:

$$R = \frac{T}{S} = \frac{\mu_{eff}(\bar{\varepsilon})L}{s_{eff}(\bar{\varepsilon})L} = \frac{\mu_{eff}(\bar{\varepsilon})}{s_{eff}(\bar{\varepsilon})}.$$

3. The method according to claim 1, wherein the sample is a breast and a volumetric breast density is estimated using the R image of the breast.

4. The method according to claim 3, wherein the volumetric breast density is defined as:

$$m(x, y) = \frac{L_g}{L} = \frac{L_g}{L_g + L_f}$$

on a pixel base for describing a volumetric proportion of glandular tissue or its complementary 1−m(x,y) for describing a volumetric proportion of fat tissue;

(x,y) is spatial coordinates of a pixel;

$L_g$ and $L_f$ are a thicknesses of the glandular tissue and the fat tissue along the X-ray beam, respectively and L is a total compression thickness wherein the volumetric breast density of a whole breast is given by averaging m over the whole breast region:

$$VBD = \frac{\sum_{x,y} m(x, y)}{N},$$

where VBD represents the volumetric breast density and N is pixel numbers of a breast region.

5. The method according to claim 4, wherein a connection between an R value and a pixel-wise volumetric breast density is given by:

$$m = \frac{1}{1 - \frac{\left(\frac{R}{R_g} - 1\right)}{\left(\frac{R}{R_f} - 1\right)}\frac{\mu_g}{\mu_f}},$$

which is deduced by a physical definition of R with a two-material composition assumption, $$R = \frac{T}{S} = \frac{\mu_g L_g + \mu_f L_f}{s_g L_g + s_f L_f} = \frac{\mu_g mL + \mu_f(1-m)L}{s_g mL + s_f(1-m)L};$$

$$R_g = \frac{\mu_g}{s_g} \text{ and } R_f = \frac{\mu_f}{s_f}$$

are defined as R values for 100% glandular tissue and 100% fat tissue, respectively;
  µ is an effective attenuation coefficient and S is the generalized scattering parameter; and
  subscripts g and f represent the glandular tissue and the fat tissue, respectively.

6. The method according to claim 5, wherein the following relationship is always true, $$R_g < R < R_f$$

which implies that the R value of the glandular tissue is smaller than the fat tissue, if a tissue is a mixture of the glandular tissue and the fat tissue, the tissue's R value falls in between.

7. The method according to claim 3, which further comprises:
  estimating the volumetric breast density using a histogram of the R image, a normalized histogram of the R image is noted as H(R), a distribution of H(R) is usually an asymmetric Gaussian distribution and any possible asymmetry is due to a fact that volumes of glandular tissue and fat tissue are different; and
  implying the volumetric breast density in a distribution, a nth moment of the distribution reveals information of breast density, including a skewness (a third moment):

$$\gamma = \frac{E[(R - \mu_R)^3]}{(E[(R - \mu_R)^2])^{3/2}},$$

gives an estimation of how dominant the glandular tissue or the fat tissue is in a whole breast; and
  R here represents a random variable and $\mu_R$ is a mean value of the R image.

8. The method according to claim 7, wherein an actual number of a breast density calculated by dynamically determining $R_g$ and $R_f$ from the histogram H(R) of the R image which is described as following:
  (1) a peak position $R_{peak}$ which gives a maximal H(R) is first decided;
  (2) the histogram H(R) is divided into left and right parts by $R_{peak}$, these two parts of the histogram are considered separately, for each half, the distribution is mirrored around a peak value to form a symmetric Gaussian distribution and then a Gaussian fitting is applied to two resulting Gaussian distributions and their standard deviations $\sigma_g$ and $\sigma_f$ are calculated respectively, wherein $R_g$ and $R_f$ are decided using the Nσ criteria;

$$R_g = R_{peak} - N\sigma_g$$

$$R_f = R_{peak} + N\sigma_f \qquad (14)$$

where N is a positive integer; with the determined $R_g$ and $R_f$, a 3D volumetric breast density VBD of the whole breast is calculated by weighting a normalized histogram H(R) using an m value;

$$VBD = \sum_R m(R) \cdot H(R).$$

9. The method according to claim 8, wherein N=3 is considered to give a best approximation of the $R_g$ and $R_f$ when noises are present.

10. The method according to claim 1, which further comprises obtaining the absorption signal and the small-angle scattering signal from an arrangement for X-rays, for obtaining quantitative X-ray images from a sample including:
  a) an X-ray source;
  b) a grating set-up selected from the group consisting of a three gratings set-up with grating G0, G1 and G2 or a two gratings set-up with the grating G1 and G2;
  c) a position-sensitive detector with spatially modulated detection sensitivity having a number of individual pixels;
  d) means for recording the images of the position-sensitive detector;
  e) means for evaluating intensities for each pixel in a series of images, in order to identify characteristics of the sample for each individual pixel as an absorption dominated pixel and/or a differential phase contrast dominated pixel and/or an X-ray scattering dominated pixel;
  wherein the series of images is collected by continuously or stepwise rotating from 0 to IF or 2π either the sample or the arrangement and the X-ray source relative to the sample.

11. The method according to claim 10, which further comprises operating the gratings either in a so-called "near field regime" or in a "Talbot-regime".

12. The method according to claim 11, wherein for near-field-regime operation, a distance between the gratings D1 and D2 is chosen freely within a regime,
  and for the Talbot-regime is chosen according to $$D_{n,sph} = \frac{L \cdot D_n}{L - D_n} = \frac{L \cdot n \cdot p_1^2 / 2\eta^2 \lambda}{L - n \cdot p_1^2 / 2\eta^2 \lambda}$$

where n=1, 3, 5 . . . , and $$\eta = \begin{cases} 1 & \text{if the phase shift of } G_1 \text{ is } (2l-1)\frac{\pi}{2}, \quad p_2 = \frac{L + D_{n,sph}}{L} p_1 \\ 2 & \text{if the phase shift of } G_1 \text{ is } (2l-1)\pi, \quad p_2 = \frac{L + D_{n,sph}}{L} \frac{p_1}{2}, \end{cases}$$

where l=1, 2, 3 . . . , $D_n$ is an odd fractional Talbot distance when a parallel X-ray beam is used, while $D_{n,sph}$ is that when a fan or cone X-ray beam is used, L is here a distance between the X-ray source and the grating G1.

13. The method according to claim 10, wherein the grating G1 is a line grating G1 either formed as an absorption grating or a phase grating, the phase grating is a low absorption grating but generating a considerable X-ray phase shift, preferably of π or odd multiples thereof.

14. The method according to claim 10, wherein the grating G2 is a line grating having a high X-ray absorption contrast with its period being a same as that of a self-image of the grating G1; the grating G2 being placed closely in front of the position-sensitive detector with its lines parallel to those of the grating G1.

15. The method according to claim 10, wherein phase stepping is performed by a shift of one of the gratings with respect to other ones of the gratings.

16. The method according to claim 10, wherein the grating set-up is manufactured by planar technology.

17. A system for quantitative radiology of a sample, such as a breast in a mammographic investigation, the system comprising:
means for evaluating recorded radiographic images, a material or material composition of the sample being determined via a radiographic approach by using a ratio of an absorption signal and a small-angle scattering signal of the underlying sample, wherein the absorption signal and the small-angle scattering signal are obtained from X-ray investigations based on grating-based interferometry, analyzer-crystal-based imaging, coded aperture imaging or imaging technique that is enabled to record absorption signals and small-angle scattering signals.

18. The system according to claim 17, further comprising an X-ray configuration, wherein the absorption signal and the small-angle scattering signal are obtained from an arrangement for X-rays, for obtaining quantitative X-ray images from the sample, said X-ray system configuration, containing:
an X-ray source;
a grating setup selected from the group consisting of a three gratings set-up with grating G0, G1 and G2 and a two gratings set-up with said grating G1 and G2;
a position-sensitive detector with spatially modulated detection sensitivity having a number of individual pixels;
means for recording the images of said position-sensitive detector; and
means for evaluating intensities for each pixel in a series of images, in order to identify characteristics of the sample for each said individual pixel as an absorption dominated pixel and/or a differential phase contrast dominated pixel and/or an X-ray scattering dominated pixel, wherein the series of images is collected by continuously or stepwise rotating from 0 to $\pi$ or $2\pi$ either the sample or said X-ray configuration and said X-ray source relative to the sample.

19. The system according to claim 18, wherein said grating G1 is a line grating G1 either formed as an absorption grating or a phase grating, said phase grating is a low absorption grating but generating a considerable X-ray phase shift, and preferably of $\pi$ or odd multiples thereof.

20. The method according to claim 18, wherein said grating G2 is a line grating having a high X-ray absorption contrast with its period being a same as that of a self image of said grating G1, said grating G2 being placed closely in front of said position-sensitive detector with its lines parallel to those of said grating G1.

21. The system according to claim 18, wherein phase stepping is performed by a shift of one of said gratings with respect to other ones of said gratings.

22. The system according to claim 18, wherein said grating setup is manufactured by planar technology.

23. The system according to claim 18, wherein the x-rays are hard X-rays.

24. The system according to claim 17, wherein the system is operated either in a so-called "near field regime" or in a "Talbot-regime".

25. The system according to claim 24, wherein for near-field-regime operation, a distance between said gratings D1 and D2 is chosen freely within a regime, and for the Talbot-regime is chosen according to $$D_{n,sph} = \frac{L \cdot D_n}{L - D_n} = \frac{L \cdot n \cdot p_1^2 / 2\eta^2 \lambda}{L - n \cdot p_1^2 / 2\eta^2 \lambda}$$

where n=1, 3, 5 . . . , and $$\eta = \begin{cases} 1 & \text{if the phase shift of } G_1 \text{ is } (2l-1)\frac{\pi}{2}, \quad p_2 = \frac{L + D_{n,sph}}{L} p_1 \\ 2 & \text{if the phase shift of } G_1 \text{ is } (2l-1)\pi, \quad p_2 = \frac{L + D_{n,sph}}{L} \frac{p_1}{2}, \end{cases}$$

where l=1, 2, 3 . . . , $D_n$ is an odd fractional Talbot distance when a parallel X-ray beam is used, while $D_{n,sph}$ is that when a fan or cone X-ray beam is used, L is here a distance between said x-ray source and said grating G1.

* * * * *